United States Patent
Almasoud

(10) Patent No.: US 11,103,338 B2
(45) Date of Patent: Aug. 31, 2021

(54) POST-SURGICAL HEALING ACCELERATOR

(71) Applicant: Imam Abdulrahman Bin Faisal University, Dammam (SA)

(72) Inventor: Naif Nasser Almasoud, Dammam (SA)

(73) Assignee: Imam Abdulrahman Bin Faisal University, Dammam (SA)

(*) Notice: Subject to any disclaimer, the term of this patent is extended or adjusted under 35 U.S.C. 154(b) by 0 days.

(21) Appl. No.: 15/823,975

(22) Filed: Nov. 28, 2017

(65) Prior Publication Data

US 2018/0263751 A1   Sep. 20, 2018

Related U.S. Application Data

(60) Provisional application No. 62/471,106, filed on Mar. 14, 2017.

(51) Int. Cl.
| | |
|---|---|
| *A61F 2/00* | (2006.01) |
| *A61L 15/44* | (2006.01) |
| *A61K 47/50* | (2017.01) |
| *A61L 31/16* | (2006.01) |
| *A61L 27/38* | (2006.01) |
| *A61L 31/00* | (2006.01) |
| *A61F 13/00* | (2006.01) |
| *A61L 27/54* | (2006.01) |
| *A61B 17/00* | (2006.01) |

(52) U.S. Cl.
CPC ...... *A61F 2/0063* (2013.01); *A61F 13/00012* (2013.01); *A61K 47/50* (2017.08); *A61L 15/44* (2013.01); *A61L 27/38* (2013.01); *A61L 27/54* (2013.01); *A61L 31/005* (2013.01); *A61L 31/16* (2013.01); *A61B 2017/00004* (2013.01); *A61B 2017/00893* (2013.01); *A61L 2300/412* (2013.01); *A61L 2300/602* (2013.01); *A61L 2300/64* (2013.01); *A61L 2430/32* (2013.01)

(58) Field of Classification Search
None
See application file for complete search history.

(56) References Cited

U.S. PATENT DOCUMENTS

| | | | |
|---|---|---|---|
| 2008/0109070 A1* | 5/2008 | Wagner | A61L 27/3843 623/1.41 |
| 2011/0034388 A1 | 2/2011 | Cornwell et al. | |
| 2014/0356331 A1* | 12/2014 | Badylak | A61L 27/3633 424/93.7 |

FOREIGN PATENT DOCUMENTS

| | | |
|---|---|---|
| CN | 102302807 A | 1/2012 |
| CN | 102552997 A | 7/2012 |
| CN | 103316379 B | 6/2015 |
| KR | 10-1495281 B1 | 2/2015 |
| WO | WO 2016/004212 A1 | 1/2016 |

OTHER PUBLICATIONS

Dabin Wang, et al., "Experimental study on bone marrow mesenchymal stem cells seeded in chitosan-alginate scaffolds for repairing spinal cord injury", Zhongguo Xiu Fu Chong Jian Wai Ke Za Zhi, vol. 24, No. 2, Feb. 2010, pp. 190-196 (Abstract only).

Carole E. Schanté, et al., "Chemical modifications of hyaluronic acid for the synthesis of derivatives for a broad range of biomedical applications", Carbohydrate Polymers, vol. 85, Jun. 2011, pp. 469-489.

* cited by examiner

*Primary Examiner* — Erin M. Bowers
(74) *Attorney, Agent, or Firm* — Oblon, McClelland, Maier & Neustadt, L.L.P.

(57) ABSTRACT

A post-surgical healing accelerator (PSHA) device for tissue and nerve repair at an injury site. The device includes (a) a substrate, (b) a scaffold disposed on a surface of the substrate, and (c) a population of cells attached to the scaffold. The scaffold comprises at least one modified polymer selected from a modified collagen, a modified gelatin, a modified alginate, a modified cellulose, a modified hyaluronic acid, and others, with (i) modifications configured to increase an interaction between the scaffold and the cells, (ii) modifications configured to increase an association of the at least one modified polymer with the substrate, and (iii) a combination of (i) and (ii). The cells attached to the scaffold are configured to carry out tissue and/or nerve repair at an injury site of a subject through at least one of growth, differentiation, and migration following an application of the device to the injury site of the subject.

20 Claims, No Drawings

POST-SURGICAL HEALING ACCELERATOR

CROSS REFERENCE TO RELATED APPLICATIONS

This application claims the benefit of U.S. Provisional Application No. 62/471,106 filed Mar. 14, 2017, which is incorporated herein by reference in its entirety.

BACKGROUND OF THE INVENTION

Technical Field

The present disclosure relates to a post-surgical healing accelerator (PSHA) device that can be applied to an injury site in a human or animal for tissue and nerve repair.

Brief Summary of the Invention

The present disclosure relates to a device that includes (a) a substrate, (b) a scaffold disposed on a surface of the substrate, and (c) a first population of cells attached to the scaffold, wherein the scaffold comprises at least one modified first polymer selected from the group consisting of a modified keratin, a modified collagen, a modified elastin, a modified fibrin, a modified thrombin, a modified fibronectin, a modified gelatin, a modified alginate, a modified pectin, a modified cellulose, a modified hyaluronic acid, a modified laminin, and a modified vitronectin, wherein the at least one modified first polymer comprises at least one modification selected from the group consisting of (i) at least one modification configured to increase an interaction between the scaffold and the first population of cells, (ii) at least one modification configured to increase an association of the at least one modified first polymer with the substrate, and (iii) a combination of (i) and (ii), and wherein the first population of cells attached to the scaffold are configured to carry out tissue and/or nerve repair at an injury site of a subject through at least one of growth, differentiation, and migration following an application of the device to the injury site of the subject.

In one or more embodiments, the substrate comprises at least one non-resorbable material.

In one or more embodiments, the at least one non-resorbable material is selected from the group consisting of polypropylene, polyester, PTFE (polytetrafluoroethylene), polyethylene, polystyrene, PET (polyethylene terephthalate), polyimide, PEN (polyethylene naphthalate), polycarbonate, a metal, an alloy, and a non-woven fabric.

In one or more embodiments, the substrate comprises at least one resorbable material.

In one or more embodiments, the at least one resorbable material is selected from the group consisting of cellulose, polyglycolic acid, poly-γ-glutamic acid, poly-1-lactic:acid, polyglactin 910, a polyhydroxylalkaoate derivative, a human amniotic membrane, a cow amniotic membrane, pig collagen, fibronectin, and dextran.

In one or mare embodiments, the substrate is in a form of a mesh with a pore size of 1-5 mm and a weight of 10-50 g/m$^2$, and the mesh has a coating selected from the group consisting of a coating of collagen, a coating of autologous platelets and blood plasma, and a coating of cross-linked fatty acids and/or glycerides.

In one or more embodiments, the substrate is in a form of a mesh, and the mesh is coated with or incorporated by a plurality of at least one nanoparticle selected from the group consisting of a superparamagnetic iron oxide nanoparticle, a graphene oxide nanoparticle, a silver nanoparticle, and a titanium dioxide nanoparticle.

In one or more embodiments, the first population of cells are at least one selected from the group consisting of embryonic stem cells, adult or embryonic mesenchymal stem cells (MSC), hematopoetic stem cells, periodontal ligament stem cells, undifferentiated cells, pluripotent cells, omnipotent cells, and umbilical cord blood cells.

In one or more embodiments, the at least one modification of (i) in the at least one modified first polymer is configured to confer a positive charge to or increase a positive charge in the at least one modified first polymer.

In one or more embodiments, the at least one modification of (i) in the at least one modified first polymer comprises at least one covalently linked polyamine.

In one or more embodiments, the at least one covalently linked polyamine is at least one selected from the group consisting of putrescine, cadaverine, spermidine, spermine, ethylene diamine, 1,3-diaminopropane, hexamethylenediamine, piperazine, cyclen, cyclam, poly-L-lysine, and polyethyleneimine. In one or more embodiments, the at least one modified first polymer is at least one selected from the group consisting of a modified alginate, a modified hyaluronic acid, a modified gelatin, and a modified collagen.

In one or more embodiments, the at least one modification of (i) in the at least one modified first polymer comprises a first molecular moiety configured to bind to a surface protein of the first population of cells.

In one or more embodiments, the at least one modified first polymer is at least one selected from the group consisting of alginate and hyaluronic acid, and the first molecular moiety is at least one peptide conjugated to the alginate and/or the hyaluronic acid and configured to bind to the surface protein of the first population of cells.

In one or more embodiments, the surface protein is a cell adhesion protein selected from the group consisting of an immunoglobulin, an integrin, a cadherin, and a selectin.

In one or more embodiments, the at least one modification of (ii) in the at least one modified first polymer comprises a second molecular moiety, and the substrate comprises or is modified to comprise a third molecular moiety, and the scaffold is disposed on the surface of the substrate via a bond between the second molecular moiety and the third molecular moiety.

In one or more embodiments, the at least one modified first polymer is covalently bonded to the substrate.

In one or more embodiments, the at least one modified first polymer of the scaffold is a composite modified polymer comprising, a plurality of constituent modified polymers cross-linked with one another, wherein the composite modified polymer comprises (i) at least one modification configured to increase an interaction between the scaffold and the first population of cells and (ii) at least one modification configured to increase an association of the composite modified polymer with the substrate, and wherein not all of the modifications of (i) and (ii) reside in any one constituent modified polymer.

In one or more embodiments, the device further comprises a first hydrogel comprising a second polymer and at least one agent selected from the group consisting of a growth factor, an angiogenic factor, a differentiation factor, a cytokine, an interleukin, a chemokine, an extracellular matrix protein, a nucleic acid, a blood and serum protein, a hormone, a vitamin, an accelerator of cell migration, an anti-oxidant, a hemostatic agent, an antimicrobial agent, an extracellular antibody, and a chemotherapeutic agent, wherein the first hydrogel is disposed on the scaffold comprising the first population of cells attached to the scaffold.

In one or more embodiments, the second polymer is at least one selected from the group consisting of fibrin glue, hyaluronic acid, gelatin, collagen, alginate, cellulose, pectin, Matrigel, and silk fibrils.

In one or more embodiments, the second polymer is covalently linked to the at least one agent.

In one or more embodiments, the device further comprises a second hydrogel comprising a third polymer and a second population of cells, wherein the second hydrogel is separated from the first hydrogel via at least one microporous membrane, wherein the at least one microporous membrane is configured to block contacting of the second population of cells in the second hydrogel with the first population of cells while allowing an exchange of non-cell contents between the first hydrogel and the second hydrogel.

In one or more embodiments, the second population of cells are non-dividing cells.

In one or More embodiments, the second population of cells comprise transfected or transduced cells harboring at least one expression vector containing at least one nucleic acid sequence encoding at least one protein or peptide.

In one or more embodiments, the third polymer is at least one selected from the group consisting of fibrin glue, hyaluronic acid, gelatin, collagen, alginate, cellulose, pectin, Matrigel, and silk fibrils.

In one or more embodiments, the device further comprises at least one rigidifying structural element configured to stabilize, immobilize, shape, and/or form-fit the device at the injury site following the application of the device to the injury site.

In one or more embodiments, the at least one rigidifying structural element is at least one selected from the group consisting of a pin, a stent, a screw, a plate, a bar, a cast, and a splint.

The foregoing paragraphs have been provided by way of general introduction, and are not intended to limit the scope of the following claims. The described embodiments, together with further advantages, will be best understood by reference to the following detailed description.

DETAILED DESCRIPTION OF THE EMBODIMENTS

The present disclosure relates to a device that includes (a) a substrate, (b) a scaffold disposed on a surface of the substrate, and (c) a first population of cells attached to the scaffold, wherein the scaffold comprises at least one modified first polymer selected from the group consisting of a modified keratin, a modified collagen, a modified elastin, a modified fibrin, a modified thrombin, a modified fibronectin, a modified gelatin, a modified alginate, a modified pectin, a modified cellulose, a modified hyaluronic acid, a modified laminin, and a modified vitronectin, wherein the at least one modified first polymer comprises at least one modification selected from the group consisting of (i) at least one modification configured to increase an interaction between the scaffold and the first population of cells, (ii) at least one modification configured to increase an association of the at least one modified first polymer with the substrate, and (iii) a combination of (i) and (ii), and wherein the first population of cells attached to the scaffold are configured to carry out tissue and/or nerve repair at an injury site of a subject through at least one of growth, differentiation, and migration following an application of the device to the injury site of the subject.

The substrate may comprise one or more non-resorbable (or non-absorbable) materials, one or more resorbable materials, or mixed non-resorbable and resorbable materials.

Resorbable materials of the substrate can be broken down by the processes of hydrolysis or proteolytic enzymatic degradation taking place after the device is applied to the injury site of the subject, e.g. a human or an animal. These chemical processes dissolve, degrade, or disintegrate the substrate in the body of the subject, eliminating the need for removal of the substrate. The time between the application of a resorbable substrate and the time that the resorbable substrate dissolves depends on the mass and resorbable material of the substrate. For example, a resorbable substrate may dissolve in as little as less than a week or may last for up to three, five, or ten weeks. The selection of suitable resorbable material for the substrate may be based on the subject's medical history (e.g. whether the subject has had any prior adverse reaction to or rejection of the material), the type of injury and the length of time the device and hence the substrate need to remain in place.

Non-limiting examples of non-resorbable materials include polypropylene, polyester, PTFE (polytetrafluoroethylene), polyethylene, polystyrene, PET (polyethylene terephthalate), polyimide, PEN (polyethylene naphthalate), polycarbonate, a metal, an alloy, and a non-woven fabric. Non-limiting examples of resorbable materials include cellulose, polyglycolic acid, poly-γ-glutamic acid, poly-1-lactic acid, polyglactin 910, a polyhydroxylalkaoate derivative (e.g. poly-4-hydroxybutyrate), a human amniotic membrane, a cow amniotic membrane, pig collagen, fibronectin, and dextran.

The substrate may be in a form of a mesh, a dressing, a gauze, a web, a film, a patch, or a sheath. In a preferred embodiment, the substrate is a mesh substrate, e.g. a polypropylene mesh, a polyester mesh, a PTFE mesh, a polyglycolic acid mesh, a poly-1-lactic acid mesh, a polyglactin 910 (Vicryl™, Ethicon, Somerville, N.J.) mesh, a polyhydroxylalkaoate derivatives mesh, a polypropylene/PTFE composite mesh, a polypropylene/cellulose mesh, a polypropylene/Seprafilm® mesh (e.g. Sepramesh® (Genzyme, Cambridge, Mass.) and Sepramesh® IP (Genzyme, Cambridge, Mass.)), a polypropylene/Vicryl mesh (e.g. Vypro™ (Ethicon, Somerville, N.J.) and Vypro™ II (Ethicon, Somerville, N.J.)), a polypropylene/Monocryl(poliglecaprone) mesh (e.g. Ultrapro® (Ethicon, Somerville, N.J.)), and a polyester/collagen mesh (e.g. Parietex® Composite (Sofradim, Trévoux, France)).

Pore size (porosity) is the main determinant of tissue reaction. Pores of a mesh substrate are preferably more than 75 μm in order to allow infiltration by macrophages, fibroblasts, blood vessels and collagen. Mesh substrates with larger pores (e.g. 1-5 mm, or 2-4 mm) allow increased soft tissue in-growth and are more flexible because of the avoidance of granuloma bridging. Granulomas normally form around individual mesh fibers as part of the foreign body reaction. Bridging describes the process whereby individual granulomas become confluent with each other and encapsulate the entire mesh substrate. This may lead to a stiff scar plate and a reduced flexibility and elasticity of the mesh substrate. In some embodiments, the pore size of the mesh substrate is 75 μm-5 mm, 100 μm-3 mm, 200 μm-2 mm, 400 μm-2 mm, 600 μm-1.5 mm, 800 μm-1.5 mm, 1 mm-5 mm, or 2 mm-4 mm. The weight of the mesh substrate is 10-150 g/m$^2$, 30-120 g/m$^2$, 50-100 g/m$^2$, or 70-90 g/m$^2$. The linear mass density of the mesh fibers of the mesh substrate is in the range of 100-500 denier, 150-450 denier, or 200-400 denier. Heavier mesh substrates have a higher tensile strength derived from a larger mass of material, which may activate a profound tissue reaction and dense scarring. When a less pronounced foreign body reaction and more elasticity of the mesh substrates are desired, light-weight mesh substrates of 10-50 g/m$^2$, 20-40 g/m$^2$ are preferred.

Since the material for the substrate, including the mesh substrate, may not be biologically inert, a foreign body reaction may be triggered when the device is applied to or implanted in the injury site of the subject. The foreign body reaction can involve inflammation, fibrosis, calcification, thrombosis and formation of granulomas, and the extent of the reaction is affected by the amount of the material present, and in the case of a mesh substrate, the pore size of the mesh substrate. As described above, a mesh substrate with small pores develops stiff scar plates which are avoided in a mesh substrate with larger pores where there is a gap between the granulomas. Besides selecting a large pore size (e.g. 1-5 mm, or 2-4 mm) when possible, the substrate material, e.g. the mesh polymers, may be modified, in various ways to decrease the foreign body reaction and increase biocompatibility. In one embodiment, the substrate, preferably the mesh substrate, may be coated with collagen, for example, to decrease visceral adhesion following intraperitoneal implantation of the mesh substrate (See Collagen/Polypropylene composite mesh biocompatibility in abdominal wall reconstruction, Lukasiewicz A, Skopinska-Wisniewska J, Marszalek A, Molski S, Drewa T, Plast Reconstr Surg. 2013 May; 131(5):731e-40e, incorporated herein by reference in its entirety). In another embodiment, the substrate, preferably the mesh substrate, may be coated with autologous platelets and blood plasma to increase the biocompatibility of the (mesh) substrate material (See Coating with Autologous Plasma Improves Biocompatibility of Mesh Grafts In Vitro: Development Stage of a Surgical Innovation, Holger Gerullis, Evangelos Georgas, Christoph Eimer, Christian Arndt, Dimitri Barski, Bernhard Lammers, Bernd Klosterhalfen, Mihaly Borós, and Thomas Otto, BioMed Research International Volume 2013 (2013), Article ID 536814, 6 pages, incorporated by reference in its entirety). In still another embodiment, the substrate, preferably the mesh substrate, may be coated with cross-linked fish oil comprising cross-linked fatty acids and/or glycerides to provide anti-inflammatory, non-inflammatory, and anti-adhesion functionality, as disclosed in U.S. Pat. No. 8,574,627 B2, incorporated herein by reference in its entirety.

In some embodiments, nanoparticles may be incorporated into or coated onto the (mesh) substrate material to confer advantageous therapeutic, diagnostic, and biocompatibility properties. For example, superparamagnetic iron oxide nanoparticles may be integrated into the mesh polymer of the substrate such that the mesh substrate of the device becomes visible in magnetic resonance imaging (MRI) (See Investigation of superparamagnetic iron oxide nanoparticles for MR-visualization of surgical implants, Slabu I, Guntherodt G, Schmitz-Rode T, Hodenius M, Kramer N, Donker H, Krombach G A, Otto J. Klinge U, Baumann M, Curr Pharm Biotechnol. 2012 March; 13(4):545-51, incorporated herein by reference in its entirety). For another example, graphene oxide and silver nanoparticles may be incorporated into the mesh polymer of the substrate to stop bleeding and disinfect the wound at the injury site. For still another example, the mesh substrate may be coated with high-purity and adherent titanium dioxide nanoparticles for improved biocompatibility.

In other embodiments, the (mesh) substrate may have microstructural features that advantageously enhance the fitting and spreading of the scaffold comprising the first population of cells for tissue/nerve repair over the injury site. For example, the surface of the substrate facing the injury site may have a plurality of concave, convex, ridge, or cylindrical shaped micro-structures with a diameter of 0.1-5 mm, 0.5-3 mm, or 1-2 mm, preferably custom designed and fabricated based on the topography of the surface of the injury site, such that the scaffold comprising the first population of cells for the tissue/nerve repair may have the best possible form-fitting for the injury site. The micro-structures may be formed with microthreads extending from the surface of the substrate at various lengths and having a diameter of 5-1000 microns, 10-800 microns, 50-600 microns, 100-500 microns, 150-400 microns, or 200-300 microns. Alternatively, the surface of the substrate may have a layer of fillers that protrude from the surface of the substrate at various heights to form a desired pattern of concave, convex, ridge, and/or cylindrical shaped topography to achieve the best possible form-fitting between the scaffold and the injury site. In a preferred embodiment, the microthreads and the fillers are made of or coated with one or more biocompatible polymers such as alginate, hyaluronic acid, and collagen.

In the device, the scaffold is disposed on the surface of the substrate that provides support for the scaffold. The scaffold comprises at least one modified first polymer, which is preferably a modified keratin, a modified collagen, a modified elastin, a modified fibrin, a modified thrombin, a modified fibronectin, a modified gelatin, a modified alginate, a modified pectin, a modified cellulose, a modified hyaluronic acid, a modified laminin, a modified vitronectin, and combinations thereof, more preferably a modified alginate, a modified hyaluronic acid, a modified collagen, and combinations thereof.

In some embodiments, the device does not contain chitosan in any part of the device, e.g. the substrate, the scaffold, and/or the hydrogels described below.

When the scaffold comprises two or more modified polymers, the constituent modified polymers may be associated with each other physically, e.g. by electrostatic interaction, by weaving or bundling of the polymer filaments, or by simple mixing of the polymers, or the constituent modified polymers may be associated with each other by covalent bonds formed by a chemical reaction, e.g. a cross-linking reaction mediated by UV or a chemical cross-linking agent. Non-limiting examples of the chemical cross-linking agent include glutaraldehyde, carbodiimides, bisdiazobenzidine, N-maleimidobenzoyl-N-hydroxysuccinimide ester, butanediol diglycidyl ether (BDDE), divinylsulfone, bis(sulfosuccinimidyl)suberate (BS$^3$), 3,3"-dithiobis(sulfosuccinimidyl) propionate (DTSSP), and 2-methylsuberimidate (DMS).

The modified polymer of the scaffold may be disposed on the surface of the substrate by dipping or immersing the substrate in a solution of the modified polymer, by spraying a solution of the modified polymer onto the surface of the substrate, or by brushing the surface of the substrate with a solution of the modified polymer. The substrate is preferably sterilized, for example, by autoclave or with alcoholic solvents (e.g. 75% ethanol) before its surface is coated or deposited with the modified polymer solution. The modified polymer in the solution may be non-cross-linked, or may be preferably cross-linked by UV or a chemical cross-linking agent prior to its disposition on the surface of the substrate. In one embodiment, the disposition of the modified polymer on the surface of the substrate is carried out only once followed by drying of the modified polymer solution present on the surface of the substrate. In another embodiment, the disposition of the modified polymer on the surface of the substrate is carried out multiple times, i.e. one or more rounds of subsequent disposition and drying of the modified polymer solution on the surface of the substrate are carried out following the first drying of the modified polymer solution on the surface of the substrate. When multiple dispositions of the modified polymer on the surface of the substrate are implemented, the same modified polymer or mixture of modified polymers may be used at each disposition, or different modified polymers or different mixtures of modified polymers may be used at various dispositions. The drying may be accomplished by air drying or by freeze drying. In some embodiments, following the final drying of the modified polymer solution on the surface of the substrate, the substrate/modified polymer scaffold composite may be sterilized, for example, by UV irradiation, alcoholic solvent (e.g. 75% ethanol) treatment, or autoclave prior to loading the first population of cells onto the scaffold.

In some embodiments, different modified polymers, preferably different ionic modified polymers (e.g. modified negatively charged hyaluronic acid and modified positively charged hyaluronic acid), may be disposed on the surface of the substrate using the layer-by-layer deposition technique to obtain a multi-layered modified polymer film serving as the scaffold on the surface of the substrate. Layer-by-layer (LbL) deposition is a thin film fabrication technique. The film is formed by depositing alternating layers of oppositely charged materials with wash steps in between. This can be accomplished by using various techniques such as immersion, spin, spray, electromagnetism, or fluidics. See Layer-by-layer deposition of hyaluronic acid and poly-L-lysine for patterned cell co-cultures, Khademhosseini A, Suh K Y, Yang J M, Eng G, Yeh J, Levenberg S, Langer R, Biomaterials. 2004 August; 25(17):3583-92; Micropatterned cell co-cultures using layer-by-layer deposition of extracellular matrix components, Junji Fukuda, Ali Khademhosseini, Judy Yeh, George Eng, Jianjun Cheng, Omid C. Farokhzad, Robert Langer, Biomaterials, Volume 27, Issue 8, March 2006, Pages 1479-1486; Layer-by-layer films from hyaluronan and amine modified hyaluronan, Aurore Schneider, Catherine Picart, Bernard Senger, Pierre Schaaf, Jean-Claude Voegel, and Benoit Frisch, Langmuir. 2007 Feb. 27; 23(5): 2655-2662, each incorporated herein by reference in its entirety, for examples of forming polymer films using the layer-by-layer deposition technique for cell adhesion and culture.

The loading of the cells onto the scaffold may be performed by contacting the scaffold comprising the modified polymer(s) with a cell suspension containing the first population of cells, preferably for a sufficiently long period of time, for example, 1-6 hours, or 3-5 hours, to allow a maximal attachment of the cells to the scaffold. In some embodiments, the above contacting for cell attachment to the scaffold is followed by culturing the cells attached to the scaffold in vitro using the standard tissue culture conditions (e.g. incubation at 37° C. with 5-7% $CO_2$ in air) for, for example, 1-14 days, 5-10 days, or 7 days before the device is applied to an injury site for tissue and/or nerve repair.

In a preferred embodiment, the scaffold provides a three-dimensional matrix for the cells attached to the scaffold to grow in number, differentiate into a specific cell type useful for tissue and/or nerve repair at the injury site, and/or migrate to a wound margin at the injury site to integrate into the tissue and/or the nerve and accomplish the tissue and nerve repair. In some embodiments, the three-dimensional matrix of the scaffold is formed from the fibers of the modified polymer(s) and preferably in the form of a mesh, having pores with uniform or mixed circular, oval, or rectilinear pore shapes, with a pore size of 0.1-150 microns, 0.5-100 microns, 1-80 microns, 5-60 microns, 10-40 microns, or 20-30 microns, with a pore volume fraction of 40-98%, 60-95%, or 80-90% (pore volume fraction is that portion of the material occupied by the pore space). Generally speaking, the size of the pores in the scaffold will range from about one to ten times the diameter of the cells to be loaded therein. A large pore volume fraction is desirable in order to allow a cell suspension to fully penetrate the matrix and thus permit cell attachment and/or cell migration throughout the scaffold. An insufficient pore size and/or pore volume fraction will restrict cells from gaining uniform access throughout the scaffold.

The device is contemplated to carry out and/or aid in repair or amelioration of any type of damaged or defective tissue and/or the nerves thereof, for example, nervous tissue, skin, vascular tissue, cardiac tissue, pericardial tissue, muscle tissue, ocular tissue, periodontal tissue, connective tissue such as bone, cartilage (articular, meniscal, septal, tracheal), tendon, and ligament, organ tissue such as breast, pancreas, stomach, esophageal, vascular, kidney, ocular and hepatic, glandular tissue such as pancreatic, mammary, and adrenal, urological tissue such as bladder and ureter, and digestive tissue such as intestinal. The damage or defect of the tissue and/or nerve may arise from a surgical wound (e.g. from a jaw surgery, or an oral surgery), a congenital malformation, a traumatic injury, an infection, or a tumor resection.

Suitable living cells for the first population of cells to be loaded onto the scaffold to carry out the tissue/nerve repair at the injury site include, but are not limited to, epithelial cells (e.g., keratinocytes, adipocytes, hepatocytes), neurons, glial cells, astrocytes, podocytes, mammary epithelial cells, islet cells, endothelial cells (e.g., aortic, capillary and vein endothelial cells), mesenchymal cells (e.g., dermal fibroblasts, mesothelial cells, osteoblasts), smooth muscle cells, striated muscle cells, ligament fibroblasts, tendon fibroblasts, chondrocytes, fibroblasts, and any of a variety of stem cells. Also suitable for use in the first population of cells are genetically modified cells, immunologically masked cells, and the like. For example, the scaffold may be loaded with osteoblasts to repair bone defects, mesothelial cells to repair a pericardial membrane, mesothelial cells to repair the abdomen, epithelial cells to repair skin, epithelial cells to repair esophagus, and so on. Any combination of two or more cell types (e.g., two, three, four, five, six, seven, eight, nine, or ten) may be used to load onto the scaffold of the device.

In a preferred embodiment, the cells of the first population are at least one selected from the group consisting of embryonic stem cells, adult or embryonic mesenchymal stem cells (MSC), hematopoetic stem cells, periodontal ligament stem cells, undifferentiated cells, pluripotent cells, omnipotent cells, and umbilical cord blood cells, since the above cell types tend to have a high growth potential and/or a potential to differentiate into various types of specialized cells of desirable functions (e.g. T cells, B cells, muscle cells, bone cells, and neurons). Methods for isolating specific types of cells are well-known in the art.

The cells of the first population are preferably derived from the intended recipient of the device (i.e. the subject) or an allogeneic donor in order to be histocompatible with the recipient, which may be a human or an animal. Donor cells may be loaded onto the scaffold of the device directly after harvest or they can be cultured in vitro using standard tissue culture techniques before being loaded onto the scaffold. Alternatively, donor cells can be cultured following the loading onto the scaffold using standard tissue culture methods described above before the device is applied to the injury site.

In one embodiment, at least one modification in the at least one modified first polymer of the scaffold is configured to increase an interaction between the scaffold and the first population of cells. In a preferred embodiment, the at least one modification in the at least one modified first polymer is configured to confer a positive charge to or increase a positive charge in the at least one modified first polymer, particularly when the modified first polymer is at a physiological pH, e.g. pH of 6-8, 7-7.6, or 7.2-7.4, to introduce or enhance an electrostatic interaction between the modified first polymer of the scaffold and the surface (or the plasma membrane) of the first population of cells. The surface or plasma membrane of cells typically is negatively charged. This may be accomplished by conjugating one or more amines, preferably polyamines, to the first polymer of the scaffold and/or cross-linking the first polymer of the scaffold with one or more amines, preferably polyamines. A polyamine is an organic compound having two or more primary amino groups —$NH_2$. Non-limiting examples of suitable polyamines include putrescine, cadaverine, spermidine, spermine, ethylene diamine, 1,3-diaminopropane, hexamethylenediamine, piperazine, cyclen, cyclam, poly-L-lysine, and polyethyleneimine.

In a preferred embodiment, the scaffold comprises a modified alginate that is covalently bonded with one or more polyamines, preferably poly-L-lysine and/or polyethyleneimine. Exemplary methods for covalently linking alginate with poly-L-lysine or polyethyleneimine are described in Biocompatibility of alginate-poly-L-lysine microcapsules for cell therapy, Orive G, Tam S K, Pedraz J L, Hallé J P, Biomaterials. 2006 July; 27(20):3691-700. Epub 2006 Mar. 29; Novel sodium alginate/polyethyleneimine polyion complex membranes for pervaporation dehydration at the azeotropic composition of various alcohols, D Anjali Devi, Biduru Smitha, Sundergopal Sridhar, Sheetal S Jawalkar and Tejraj M Aminabhavi, Journal of Chemical Technology and Biotechnology, Volume 82, Issue 11, pages 993-1003, November 2007; Physical Properties of polyethyleneimine-alginate gels, Suhaila Mohamed and Abu Bakar Salleh, biotechnology letters 4(9): 611-614 (1982), each of which is incorporated herein by reference in its entirety.

In another preferred embodiment, the scaffold comprises a modified hyaluronic acid that is covalently linked with one or more polyamines, preferably poly-L-lysine and/or polyethyleneimine. Exemplary methods for covalently linking hyaluronic acid with polyamines are disclosed in Chemical modifications of hyaluronic acid for the synthesis of derivatives for a broad range of biomedical applications, Carole E. Schanté, Guy Zuber, Corinne Herlin, Thierry F. Vandamme, Carbohydrate Polymers 85 (2011) 469-489; Hyaluronic acid based self-assembling nanosystems for CD44 target mediated siRNA delivery to solid tumors, Shanthi Ganesh, Arun K. Iyer, David V. Morrissey, and Mansoor M. Amiji, Biomaterials. 2013 April; 34(13): 3489-3502, each of which is incorporated herein by reference in its entirety.

In still another preferred embodiment, the scaffold comprises a modified gelatin covalently linked with one or more polyamines, preferably poly-L-lysine and/or polyethyleneimine. An exemplary method of covalently linking polyethyleneimine with gelatin using EDC (1-ethyl-3-(3-dimethylaminopropyl) carbodiimide) is described in Surface Modification of Gelatin Nanoparticles with Polyethylenimine as Gene Vector, Wei-Ti Kuo, Hong-Yi Huang, Min-Ju Chou, Meng-ChaoWu, and Yi-You Huang, Journal of Nanomaterials, Volume 2011, Article ID 646538, 5 pages, incorporated herein by reference in its entirety.

In still another preferred embodiment, the scaffold comprises a modified collagen covalently linked with one or more polyamines, preferably poly-L-lysine, polyethyleneimine, ethylenediamine (EDA), and/or N,N-dimethyl-EDA. An exemplary method of making a collagen derivative with ethylenediamine (EDA) or N,N-dimethyl-EDA is described in Improving biomaterial properties of collagen films by chemical modification, Tiller J Cl, Bonner G, Pan L C, Klibanov A M, Biotechnol Bioeng. 2001 May 5; 73(3):246-52, incorporated herein by reference in its entirety.

In some embodiments, the polyamine content of the modified first polymer is 1-30%, 3-25%, 5-20%, 8-15%, or 10-12% of the total weight of the modified first polymer. A desirable polyamine content of the modified first polymer may be determined based on several factors, such as the efficiency of cell adhesion to the scaffold comprising the polyamine bonded first polymer, an acceptable level of potential toxicity of the polyamine groups in the modified first polymer to the first population of cells attached to the scaffold, and an acceptable biocompatibility level of the polyamine bonded first polymer. The polyamine content of the modified first polymer may be determined by $^1$H-NMR spectroscopy or liquid chromatography.

To increase an interaction between the scaffold and the first population of cells, in another embodiment, the at least one modified first polymer is modified to comprise a first molecular moiety configured to bind to a surface protein of the first population of cells. In a preferred embodiment, the first population of cells comprises stem cells or progenitor cells having the potential to differentiate into a specific type of cells (e.g. neurons, muscle cells, or bone cells) capable of filling a wound gap to repair the tissue and/or the nerve at the injury site, and the surface protein of the stem cells or the progenitors is one of the surface marker proteins that are only present on the surface of the stem cells or the progenitor cells but absent on the surface of the differentiated cells. The first molecular moiety on the modified first polymer of the scaffold may be a peptide conjugated to the first polymer and configured to specifically bind to the surface marker protein of the stem/progenitor cells. This is an advantageous embodiment, since only the stem cells or the progenitor cells are retained on the scaffold via the interaction between the modified first polymer and the stem/progenitor cells, and the differentiated cells derived from the stem/progenitor cells are free to migrate away from the scaffold and enter the wound margin at the injury site to make the tissue and/or nerve repair. Examples of embryonic stem cell surface markers include, without limitation, stage specific embryonic antigens (SSEAs) (e.g. SSEA-1, SSEA-3, and SSEA-4), cluster of differentiation (CD) antigens (e.g. CD324 (E-cadherin)), CD90, CD117, and CD29 ($\beta$1 integrin), and other surface antigens (e.g. TRA-1-60 and TRA-1-81). The above mentioned embryonic stem cell surface markers and peptide sequences that specifically bind to the embryonic stein cell surface markers are described in Embryonic Stem Cell Markers, Wenxiu Zhao, Xiang Ji, Fangfang Zhang, Liang Li and Lan Ma, Molecules 2012, 17, 6196-6236, incorporated herein by reference in its entirety. Once a cell surface marker is selected and the peptide binding to the cell surface marker is determined, the peptide may be conjugated to the first polymer, preferably alginate or hyaluronic acid. The methods of conjugation of alginate or hyaluronic acid to a peptide are known to a person of skill in the art. For example, a method of conjugating alginate to a synthetic peptide is disclosed in Conjugation of alginate to a synthetic peptide containing T- and B-cell epitopes as an induction for protective immunity against *Pseudomonas aeruginosa*, Farjaha A, Owlia P, Siadat S D, Mousavi S F, Shafieeardestani M, J Biotechnol. 2014 Dec. 20; 192 Pt A:240-7, incorporated herein by reference in its entirety. A method of conjugating hyaluronic acid to a peptide is described in Signal transduction of hyaluronic acid-peptide conjugate for formyl peptide receptor like 1 receptor. Oh E J, Kim J W, Kong J H, Ryu S H, Hahn S K, Bioconjug. Chem. 2008 December; 19(12):2401-8, incorporated herein by reference in its entirety. In some embodiments, the surface protein of the cells of the first population is a cell adhesion protein, such as an immunoglobulin, an integrin, a cadherin, and a selectin. When the surface protein of the first population of cells selected is an integrin, the peptide conjugated to alginate or hyaluronic acid may be, for example, an RGD tripeptide composed of L-arginine, glycine, and L-aspartic acid. The RGD tripeptide binds to nearly half of the over 20 known integrins and may promote cell attachment to the scaffold comprising the RGD-conjugated alginate or hyaluronic acid. Examples of RGD-conjugated alginates and their preparation methods for tissue engineering are disclosed in Cell-interactive alginate hydrogels for bone tissue engineering, Alsberg E, Anderson K W, Albeiruti A, Franceschi R T, Mooney D J, J Dent Res. 2001 November; 80(11):2025-9; An alginate-based hybrid system for growth factor delivery in the functional repair of large bone defects, Kolambkar Y M, Dupont K M, Boerckel J D, Huebsch N, Mooney D J, Hutmacher D W, Guldberg R E, Biomaterials. 2011 January; 32(1):65-74, each incorporated herein by reference in its entirety. Some of the stem/progenitor cell surface markers may also be cell adhesion proteins as exemplified above.

In some embodiments, the substrate and/or the modified first polymer of the scaffold may be modified to increase an association between the substrate and the modified first polymer of the scaffold. In one embodiment, the at least one modified first polymer of the scaffold comprises a second molecular moiety, and the substrate comprises or is modified to comprise a third molecular moiety, and the scaffold is disposed on the surface of the substrate via a bond between the second molecular moiety and the third molecular moiety. For example, the scaffold may comprise a modified alginate covalently conjugated to biotin as the second molecular moiety, and the substrate may comprise or may be modified to comprise a third molecular moiety capable of binding to the second molecular moiety, preferably with high affinity. For example, the substrate may comprise a polymer (e.g. cellulose) conjugated with avidin or streptavidin, or the substrate may comprise a plastic, such as polypropylene or polystyrene, of which surface is coated with avidin or streptavidin. Both avidin and streptavidin bind to biotin with high affinity. Conjugation of alginate with biotin is described by Polyak B1, Geresh S, Marks R S, Synthesis and characterization of a biotin-alginate conjugate and its application in a biosensor construction, Biomacromolecules. 2004 March-April; 5(2):389-96, incorporated herein by reference in its entirety. Conjugation of polymers, e.g. cellulose, with avidin or streptavidin is known in the art. See Generic Method for Attaching Biomolecules via Avidin—Biotin Complexes Immobilized on Films of Regenerated and Nanofibrillar Cellulose, Hannes Orelma, Leena-sisko Johansson, Hari Filpponen, Orlando J. Rojas, and Janne Laine, Biomacromolecules, 2012, 13 (9), pp 2802-2810, incorporated herein by reference in its entirety, for an example of making avidin-conjugated cellulose. Coating of a plastic surface with avidin or streptavidin is also well known in the art. As another example, the scaffold may comprise a modified alginate covalently conjugated with heparin. An exemplary method of making an alginate-heparin conjugate is disclosed by Zuo Ql, Guo R, Liu Q, Hong A, Shi Y, Kong Q, Huang Y, He L, Xue W., Heparin-conjugated alginate multilayered microspheres for controlled release of bFGF., Biomed Mater. 2015 Jun. 4; 10(3):035008, incorporated herein by reference in its entirety. The substrate may be a plastic, such as polystyrene, of which surface may be coated with a protein or peptide that binds to heparin with high affinity. Heparin binding proteins are well known in the art, including, without limitation, fibroblast growth factor, azurocidin, and pleiotrophin. The peptide may be selected based on the regions of the heparin binding proteins that confer the heparin-binding activity. The techniques of coating of a plastic surface with a protein or a peptide are also well known in the art, one of which is disclosed by Cuccuru M A I, Dessi D, Rappelli P, Fiori P L, A simple, rapid and inexpensive technique to bind small peptides to polystyrene surfaces for immunoenzymatic assays, J Immunol Methods. 2012 Aug. 31; 382(1-2):216-9, incorporated herein by reference in its entirety. As still another example, the scaffold may comprise a modified alginate covalently conjugated with a laminin peptide that binds to an integrin. An exemplary integrin-binding alginate-laminin peptide conjugate is disclosed by Yamada Y I, Hozumi K, Katagiri F, Kikkawa Y, Nomizu M, Biological activity of laminin peptide-conjugated alginate and chitosan matrices, Biopolymers. 2010; 94(6):711-20, incorporated herein by reference in its entirety. The substrate may be again a plastic whose surface is coated with the integrin protein or a peptide derived from the integrin protein that confers the binding activity.

Similar to alginate, hyaluronic acid may be conjugated to biotin or a peptide, and the scaffold may comprise a hyaluronic acid-biotin conjugate (which can be obtained commercially from Sigma-Aldrich, St. Louis, Mo., USA, for example) or a hyaluronic-peptide conjugate that binds with high affinity to the substrate comprising avidin/streptavidin or a binding partner for the peptide.

In another embodiment, the modified first polymer of the scaffold may be covalently bonded to the substrate. For example, the modified first polymer of the scaffold may be a modified hyaluronic acid covalently linked to a metal substrate or a substrate comprising a polymer such as a derivative of cellulose, a poly-vinyl alcohol, or a poly (acrylic acid). See Pitt, W., Morris, R., Mason, M., Hall, M., Luo, Y., & Prestwich, G. (2004). Attachment of hyaluronan to metallic surfaces. Journal of Biomedical Materials Research Part A, 68(1), 95-106, incorporated herein by reference in its entirety, for an example of attaching hyaluronic acid to a metal substrate. See Burns, J., Cox, S., & Walts, A. (1991), Water insoluble derivatives of hyaluronic acid. U.S. 5,017,229; Cascone, M. G., Sim, B., & Sandra, D. (1995), Blends of synthetic and natural polymers as drug delivery systems for growth hormone, Biomaterials, 16(7), 569-574, each incorporated herein by reference in its entirety, for examples of covalently linking hyaluronic acid to a polymer that may be present in the substrate.

In one embodiment, the scaffold comprises a single modified polymer with modifications configured (i) to increase an interaction between the scaffold and the first population of cells and (ii) to increase an association of the modified polymer with the substrate. For example, the modified polymer of the scaffold is a modified hyaluronic acid covalently linked with biotin, a peptide capable of binding to a surface protein of the first population of cells, and a polyamine. The multiply modified hyaluronic acid may be further cross-linked with one another to result in a higher stability.

In a preferred embodiment, the scaffold comprises two or more modified polymers mixed or, more preferably, cross-linked with one another (to likely increase the stability of the resulting composite modified polymer). The resulting composite modified polymer of the scaffold comprises modifications configured (i) to increase an interaction between the scaffold and the first population of cells and (ii) to increase an association of the composite modified polymer with the substrate, however, not all of the modifications present in the composite modified polymer reside in any one constituent modified polymer. For example, the scaffold may comprise a biotin-conjugated cellulose, an alginate conjugated to a peptide that binds, to a surface protein of cells of the first population, and a hyaluronic acid cross-linked with a polyamine, with the three modified polymers crass-linked to one another. Cross-linking of hyaluronic acid with alginate may be carried out as disclosed in Novel crosslinked alginate/hyaluronic acid hydrogels for nerve issue engineering. Min-Dan Wang, Peng Zhai, David J. Schreyer, Ruo-Shi Zheng, Xiao-Dan Sun, Fu-Zhai Cui, and Xiong-Biao Chen, Frontiers of Materials Science 7(3), 269-284, August 2013; Photocrosslinked alginate with hyaluronic acid hydrogels as vehicles for mesenchymal stem cell encapsulation and chondrogenesis, Coates E E I, Riggin C N, Fisher J P, J Biomed Mater Res A. 2013 July; 101(7):1962-70, each incorporated herein by reference in its entirety. The relative proportions of the constituent modified polymers in the composite modified polymer may vary without limitation, depending on, for example, the nature of the modifications in each constituent modified polymer, the characteristics of the first population of cells, the substrate, the desirable strength of attachment of the first population of cells to the scaffold, and the desirable strength of binding of the scaffold to the substrate. As an example, when a modified alginate and a modified hyaluronic acid form a mixed or composite modified polymer of the scaffold, the weight ratio of the modified alginate: the modified hyaluronic acid may be 10:1-1:10, 8:1-1:8, 4:1-1:4, or 2:1-1:2, however, other weight ratios may also be appropriate.

To provide an extracellular environment conducive to the growth, differentiation, and migration of the first population of cells attached to the scaffold as well as treatment of the tissue and/or nerve to be repaired, in a preferred environment, the device may further comprise a first hydrogel disposed on, or covering the scaffold comprising the first population of cells attached to the scaffold. The first hydrogel comprises a second polymer and at least one agent selected from the group consisting of a growth factor, an angiogenic factor, a differentiation factor, a cytokine, an interleukin, a chemokine, an extracellular matrix protein, a nucleic acid, a blood and serum protein, a hormone, a vitamin, an accelerator of cell migration, an anti-oxidant, a hemostatic agent, an antimicrobial agent, an extracellular antibody, and a chemotherapeutic agent. The amount of the agent in the first hydrogel may be of a physiological concentration, for example, when the agent is a growth factor, an angiogenic factor, or a hormone, or may be of an effective amount of the agent known to a skilled artisan, for example, when the agent is an accelerator of cell migration, an anti-oxidant, a hemostatic agent, an antimicrobial agent, an extracellular antibody, or a chemotherapeutic agent. Since the agents in the first hydrogel that provide treatment of the tissue and/or nerve to be repaired act locally, the amounts of those agents may be advantageously reduced as compared to the amounts when those agents are administered systemically. Doses of the various agents included in the first hydrogel will vary greatly according to the species, age, weight, size, and sex of the subject and are readily determinable by a skilled artisan.

Non-limiting examples of relevant agents include vascular endothelial cell growth factors (VEGF) (e.g., VEGF A, B, C, D, and E), platelet-derived growth factor (PDGF), insulin-like growth factor (IGF) I and IGF-II, interferons (IFN) IFN-$\alpha$, $\beta$, or $\gamma$), fibroblast growth factors (FGF) (e.g., FGF1, FGF-2, FGF-3, FGF-4-FGF-10), epidermal growth factor, keratinocyte growth factor, transforming growth factors (TGF) (e.g., TGF$\alpha$ or $\beta$), tumor necrosis factor-$\alpha$, an interleukin (IL) (e.g., IL-1, IL-2, IL-6, IL-17, IL-18), Osterix, Hedgehogs (e.g., sonic or desert), SOX9, bone morphogenetic proteins (BMP's), in particular, BMP 2, 4, 6, and (BMP-7 is also called OP-1), parathyroid hormone, calcitonin prostaglandins, ascorbic acid, CCL2 (MCP-1), CX3CL1, anti-epidermal growth factor receptor (EGFR) monoclonal antibodies (e.g. cetuximab, panitumumab, and trastuzumab), and an anti-CTLA4 monoclonal antibody (Ipilimumab).

Non-limiting examples of extracellular matrix proteins include collagen, elastin, laminin, tenascin, and fibronectin.

Non-limiting examples of blood and serum proteins include albumin, thrombospondin, van Willebrand factor, and fibulin.

The accelerator of cell migration may include an inhibitor of a microtubule-severing enzyme, an inhibitor of microtubule degradation, or an accelerator of microtubule formation. For example, the microtubule-severing enzyme may be a fidgetin-like 2 (FL2) enzyme and the inhibitor of a microtubule-severing enzyme may be an inhibitor of FL2, which may be an FL2-inhibiting antisense nucleotide (e.g., an antisense DNA) or an FL2-inhibiting siRNA.

Suitable anti-oxidants include a glycyrrhetinic acid (GA) (also known as enoxolone), a nicotinamide (also known as vitamin B3), a niacin, a vitamin A, a vitamin C, a vitamin B, or any tocopherol or tocotrienol, or a deferoxamine (also known as desferoxamine B, desferoxamine B, DFO, DFO-B, DFOA, DFB or desferal).

The hemostatic agent may be tranexamic acid, or a synthetic analog of the amino acid lysine.

The antimicrobial agent may be an antibacterial agent, an antiviral agent, an antifungal agent, and an antiparasitic agent. Non-limiting examples of the antibacterial agent (antibiotics) include 1) aminoglycosides, such as gentamycin, kanamycin, neomycin, streptomycin or tobramycin; 2) cephalosporins, such as cefaclor, cefadroxil or cefotaxime; 3) macrolides, such as azithromycin, clarithromycin, or erythromycin; 4) penicillins, such as amoxicillin, carbenicillin or penicillin; 5) peptides, such as bacitracin, polymixin B, or vancomycin; 6) quinolones, such as ciprofloxacin, levofloxacin, or enoxacin; 7) sulfonamides, such as sulfamethazole, sulfacetimide; or sulfamethoxazole; 8) tetracyclines, such as doxycycline, minocycline or tetracycline; 9) other antibiotics with diverse mechanisms of action such as rifampin, chloramphenicol, or nitrofuratoin.

Chemotherapeutic agents may be advantageously included in the first hydrogel when the injury is derived from a tumor resection. Malignant tumors that occur in soft tissue, including for example, tumors of the esophagus, stomach, colon, bladder are typically treated by tumor resection and systemic administration of anticancer drugs. Inclusion of chemotherapeutic agents in the first hydrogel can provide local high concentrations of chemotherapy, thus mitigating the toxicity associated with long term high systemic doses.

Examples of classes of chemotherapeutic agents include, without limitation, 1) alkylating agents, e.g., cyclophosphamide; 2) anthracyclines, e.g., daunorubicin, doxorubicin; 3) cycloskeletal disruptors, e.g., paclitaxel; 4) topoisomerase inhibitors, e.g., etoposide; 5) nucleotide analogues, e.g., azacitidine, fluorouracil, gemcitabine; 6) peptides, e.g., Neomycin; 7) platinum-based agents, e.g., carboplatin, cisplatin; 8) retinoids, e.g., all-trans retinoic acid; and 9) vinca alkaloids, e.g., vinblastine or vincristine.

The second polymer may be unmodified or modified, and may be the same as or different from the first polymer of the scaffold. Non-limiting examples of the second polymer include fibrin glue, hyaluronic acid, gelatin, collagen, alginate, cellulose, pectin, Matrigel, silk fibrils, and combinations thereof. When the second polymer is a combination of polymers, the polymers may be combined by simply mixing the polymers in a water solution, or by cross-linking the polymers with UV or a chemical cross-linking agent to form a cross-linked composite polymer.

In one embodiment, the preparation of the first hydrogel comprises mixing a water solution of the second polymer with the agents included in the first hydrogel.

In another embodiment, the preparation of the first hydrogel comprises covalently linking the agents included in the first hydrogel with the second polymer. The covalent linkage between the agents and the second polymer may be formed by a ligase that generates a carbon-oxygen bond, a carbon-sulfur bond, a carbon-nitrogen bond, or a carbon-carbon bond between the agents and the second polymer. Alternatively, the covalent linkage between the agents and the second polymer may be formed by a crosslinking agent (e.g., a chemical crosslinking agent or ultraviolet radiation). Covalently linking the agents with the second polymer may advantageously result in a slower and longer release of the agents at the injury site as compared to free agents non-bonded to the second polymer, since the release typically occurs when the covalent linkage (or bond) is broken down by enzymes of the recipient of the device, i.e. the subject.

In a preferred embodiment, the second polymer is alginate, and the alginate hydrogel comprising the agents described above may be prepared by mixing an alginate solution with the agents, followed by cross-linking the alginate in the presence of a divalent cation, e.g. in a calcium sulfate solution. See An Alginate-based Hybrid System for Growth Factor Delivery in the Functional Repair of Large Bone Defects, Kolambkar Y M, Dupont K M, Boerckel J D, Huebsch N, Mooney D J, Hutmacher D W, Guldberg R E, Biomaterials. 2011 January; 32(1):65-74, incorporated herein by reference in its entirety, for an exemplary method of preparing an alginate hydrogel comprising growth factors. In another preferred embodiment, the first hydrogel comprises hyaluronic acid, more preferably cross-linked hyaluronic acid (which is more stable than the non-cross-linked hyaluronic acid), as the second polymer. In still another preferred embodiment, the first hydrogel comprises cross-linked hyaluronic acid conjugated to therapeutic agents, e.g. ibuprofen, hydrocortisone, paclitaxel, proteins, antibiotics, and/or DNA. See Hyaluronic Acid Based Hydrogels for Regenerative Medicine Applications, Assunta Borzacchiello, Luisa Russo, Birgitte M. Malle, Khadija Schwach-Abdellaoui, and Luigi Ambrosio, BioMed Research International, Volume 2015 (2015), Article ID 871218, 12 pages, incorporated herein by reference in its entirety, for an exemplary hyaluronic acid hydrogel preparation method.

To promote migration of the first population of cells into the blood circulation and/or connect the first population of cells with the circulating blood, for example, to obtain nutrients, oxygen, $CO_2$, additional growth factors and/or hormones from the blood of the recipient of the device (i.e. the subject), the first hydrogel may preferably comprise angiogenic factors to promote vascularization at the injury site contacting the device. Non-limiting examples of the angiogenic factors include angiogenin, fibroblast growth factor, transforming growth factors, and vascular endothelial growth factor (VEGF).

In another embodiment, the device further comprises a second hydrogel comprising a third polymer and a second population of cells, wherein the second hydrogel is separated from the first hydrogel via at least one microporous membrane, wherein the at least one microporous membrane is configured to block contacting of the second population of cells in the second hydrogel with the first population of cells while allowing an exchange of non-cell contents between the first hydrogel and the second hydrogel. Like the second polymer in the first hydrogel, the third polymer in the second hydrogel may be at least one selected from the group consisting of fibrin glue, hyaluronic acid, gelatin, collagen, alginate, cellulose, pectin, Matrigel, and silk fibrils, preferably an alginate, preferably an hyaluronic acid, preferably a mixture or cross-linked product of alginate and hyaluronic acid. The third polymer may be an unmodified polymer, a modified polymer, or a mixture or a cross-linked product of unmodified and/or modified polymers.

In a preferred embodiment, the second hydrogel comprises the second population of cells obtained from an in vitro cell culture in a hydrogel, such that the in vitro cultured cells can be readily transferred to the device without additional culturing. Growing and maintaining a cell culture in a hydrogel is known to a person of skill in the art. See Hydrogels as Extracellular Matrix Mimics for 3D Cell Culture, Mark W. Tibbittl and Kristi S. Anseth, Biotechnol Bioeng. 2009 Jul. 1; 103(4): 655-663, incorporated herein by reference in its entirety, for a comprehensive review of using hydrogels for culturing cells. See Comparison of bone marrow cell growth on 2D and 3D alginate hydrogels, Barralet J E, Wang L, Lawson M, Triffitt J T, Cooper P R, Shelton R M, J Mater Sci Mater Med. 2005 June; 16(6): 515-9, incorporated herein by reference in its entirety, for an example of growing and maintaining a cell culture in an alginate hydrogel. See Designing scaffolds for valvular interstitial cells: cell adhesion and function on naturally derived materials, Masters K S, Shah D N, Walker G, Leinwand L A, Anseth K S, J Biomed Mater Res A. 2004 October 1; 71(1):172-80, incorporated herein by reference in its entirety, for an example of growing and maintaining a cell culture in a modified hyaluronic acid hydrogel. See Porcine aortic valve interstitial cells in three-dimensional culture: comparison of phenotype with aortic smooth muscle cells, Butcher J Tl, Nerem R M, J Heart Valve Dis. 2004 May; 13(3):478-85, incorporated herein by reference in its entirety, for an example of growing and maintaining a cell culture in a collagen hydrogel. Like the first hydrogel, the second hydrogel may further comprise substances conducive to the growth and viability of the second population of cells, such as a growth factor, an angiogenic factor, a differentiation factor, a cytokine, an interleukin, an extracellular matrix protein, a nucleic acid, a blood and serum protein, a hormone, a vitamin, an anti-oxidant, and an antimicrobial agent. The second hydrogel is preferably confined in a compartment adjacent to but separate from the first hydrogel by the microporous membranes. The volume ratio of the first hydrogel:the second hydrogel is preferably 5:1-1:1, 3:1-1:1, or 2:1-1:1.

The above is an advantageous embodiment when the first population of cells require substances (e.g. hormones, growth factors, and extracellular matrix proteins) produced by the second population of cells to grow, differentiate, and/or migrate to accomplish the tissue/nerve repair. The second hydrogel provides an environment to grow and keep viable the second population of cells, however, the second population of cells are prevented from entering the injury site or the first hydrogel and from mixing with the first population of cells because of the microporous membrane, which has a pore size smaller than the size of the cells of the first and the second populations, e.g. a pore size of 0.1-3 µm, 0.2-2.5 µm, 0.4-2 µm, or 1-1.5 µm, but big enough to allow an exchange of non-cell contents, such as water, ions, macromolecules (e.g. lipids, and proteins), small molecular weight solutes (e.g. vitamins), hormones, growth factors, etc, between the second hydrogel and the first hydrogel. In a preferred embodiment, the microporous membrane has the characteristics of a Transwell (trademark) membrane manufactured by Corning Incorporated Life Sciences (Tewksbury, Mass., USA), e.g. the membrane may be made of polyester, polycarbonate, or PTFE, coated or uncoated with collagen, with a thickness of 5-50 µm, 10-40 µm, or 20-30 µm. Thus, the first population of cells may obtain important substances produced and secreted by the second population of cells without being contaminated by the second population of cells.

The second population of cells may be of any cell type, depending on the substances (e.g. hormones, growth factors, and extracellular matrix proteins) the first population of cells need and the second population cells are able to produce and provide to the first population of cells. The second population of cells are preferably derived from the recipient of the device (i.e. the subject) or an allogeneic donor for hiscompatibility. In another preferred embodiment, the second population of cells are (irradiated) non-dividing cells to prevent growth of the second population of cells in case they accidentally leak into the first hydrogel or the injury site. In another preferred embodiment, the second population of cells are transfected or transduced (stably or transiently) with expression vectors (plasmids or viral vectors) containing nucleic acid sequences encoding the desirable substances (e.g. factors and enzymes) that are proteins or peptides.

In some embodiments, the second population of cells may be transfected or transduced to produce enzymes specifically able to break the covalent linkages between the agents and second polymer in the first hydrogel, resulting in localized release of the agents in the first hydrogel contacting the injury site. The production of the enzymes by the second population of cells may be constitutive, or more preferably inducible by, for example, an environmental stimulus (e.g. heat shock, light, or exposure to antibiotics).

To apply the device to an injury site for tissue/nerve repair, the embodiments of the device may be configured or assembled in many forms according to the size and shape of the injury site and the tissue/nerve repair that is desired. For example, the device may be (a) wrapped around a tissue that is damaged or that contains a defect; (b) placed on the surface of a tissue that is damaged or has a defect; (c) rolled up and inserted into a cavity, gap, or space in the tissue. One or more (e.g., one, two, three, four, five, six, seven, eight, nine, ten, 12, 14, 16, 18, 20, 25, 30, or more) such devices, stacked or adjacent to each other, can be used at any particular site. The device can be held in place by, for example, sutures, staples, tacks, or tissue glues or sealants known in the art. Alternatively, if, for example, packed sufficiently tightly into a defect or cavity, the device may need no securing device.

Alternatively, the device may further comprise or may be assembled in conjunction with other tissue repair materials, such as woven or non-woven meshes, dressing, bandage, pins, stents, screws, plates, patches, bars, casts, and splints, either permanently or non-permanently, by wrapping, taping, or stapling.

In a preferred embodiment, the device further comprises at least one rigidifying structural element configured to stabilize, immobilize, shape, and/or form-fit the device at the injury site, such as a broken bone, a broken jaw, and wounds from tooth extractions, periodontal surgery and implant surgery, while the cells on the scaffold perform the tissue/nerve repair. Non-limiting examples of suitable rigidifying structural elements include a pin, a stem, a screw, a plate, a bar, a cast, and a splint. For example, the device may include a plate or a cast shaped according to the contour of the injury site (e.g. a jawline when the device is used to repair a jaw wound sustained during a jaw surgery), and may be stabilized or immobilized at the injury site with a plurality of pins and screws such that a maximal contact of the scaffold to which the first population of cells are attached with the injury site is maintained throughout the duration of the tissue/nerve repair. The materials for the rigidifying structural elements preferably have sufficient mechanical strength to withstand force or pressure to stabilize, immobilize, shape, and/or form-fit the device at the injury site while being amenable to be shaped in a desired form, for example, to conform to the contour of the injury site during the fabrication of the device. Suitable materials for the rigidifying structural elements include, but are not limited to, metal (e.g. stainless steel), plastic, plaster, and fiberglass.

To achieve the best possible tissue/nerve repair results, a maximal contact of the cell-loaded scaffold or the first hydrogel covering the cell-loaded scaffold (when the device includes the first hydrogel) with the injury site is preferred.

The invention claimed is:

1. A post-surgical healing accelerator device, comprising:
  (a) a substrate in the form of a polypropylene mesh with a pore size of 1-5 mm and a weight of 10-50 g/m$^2$,
  (b) a scaffold disposed on a surface of the substrate, wherein the scaffold comprises a first layer of a putrescine-modified keratin and a second layer of a putrescine-modified hyaluronic acid, wherein the first layer is in direct and continuous contact with the substrate and the second layer coats the first layer, and at least a portion of the putrescine-modified keratin and the putrescine-modified hyaluronic acid are covalently bonded to one another through the putrescine, and
  (c) a first population of cells attached to the scaffold,
  wherein the scaffold optionally comprises at least one putrescine-modified first polymer selected from the group consisting of a modified collagen, a modified elastin, a modified fibrin, a modified thrombin, a modified fibronectin, a modified gelatin, a modified alginate, a modified pectin, a modified cellulose, a modified hyaluronic acid, a modified laminin, and a modified vitronectin,
  wherein the at least one putrescine-modified first polymer comprises at least one modification selected from the group consisting of (i) at least one modification configured to increase an interaction between the scaffold and the first population of cells, (ii) at least one modification configured to increase an association of the at least one modified first polymer with the substrate, and (iii) a combination of (i) and (ii), and wherein the first population of cells attached to the scaffold are configured to carry out tissue and/or nerve repair at an injury site of a subject through at least one of growth, differentiation, and migration following an application of the device to the injury site of the subject.

2. The device of claim 1, wherein the substrate further comprises,
a coating selected from the group consisting of a coating of collagen, a coating of autologous platelets and blood plasma, and a coating of cross-linked fatty acids and/or glycerides.

3. The device of claim 1,
wherein the mesh is coated with a plurality of at least one nanoparticle selected from the group consisting of a superparamagnetic iron oxide nanoparticle, a graphene oxide nanoparticle, a silver nanoparticle, and a titanium dioxide nanoparticle.

4. The device of claim 1, wherein the first population of cells are at least one selected from the group consisting of embryonic stem cells, adult or embryonic mesenchymal stem cells (MSC), hematopoetic stem cells, periodontal ligament stem cells, undifferentiated cells, pluripotent cells, omnipotent cells, and umbilical cord blood cells.

5. The device of claim 1, wherein the putrescine-modified hyaluronic acid comprises a first molecular moiety configured to bind to a surface protein of the first population of cells.

6. The device of claim 5,
wherein the first molecular moiety is at least one peptide conjugated to the hyaluronic acid and configured to bind to the surface protein of the first population of cells.

7. The device of claim 5, wherein the surface protein is a cell adhesion protein selected from the group consisting of an immunoglobulin, an integrin, a cadherin, and a selectin.

8. The device of claim 1, wherein the putrescine-modified keratin comprises a second molecular moiety, and the substrate comprises or is modified to comprise a third molecular moiety, and
wherein the scaffold is disposed on the surface of the substrate via a bond between the second molecular moiety and the third molecular moiety.

9. The device of claim 1, wherein the putrescine-modified keratin is covalently bonded to the substrate.

10. The device of claim 1, wherein the putrescine-modified keratin is a composite modified polymer comprising a plurality of constituent modified polymers cross-linked with one another,
wherein the composite modified polymer comprises (i) at least one modification configured to increase an interaction between the scaffold and the first population of cells and (ii) at least one modification configured to increase an association of the composite modified polymer with the substrate, and
wherein not all of the modifications of (i) and (ii) reside in any one constituent modified polymer.

11. The device of claim 1, further comprising a first hydrogel comprising a second polymer and at least one agent selected from the group consisting of a growth factor, an angiogenic factor, a differentiation factor, a cytokine, an interleukin, a chemokine, an extracellular matrix protein, a nucleic acid, a blood and serum protein, a hormone, a vitamin, an accelerator of cell migration, an anti-oxidant, a hemostatic agent, an antimicrobial agent, an extracellular antibody, and a chemotherapeutic agent,
wherein the first hydrogel is disposed on the scaffold comprising the first population of cells attached to the scaffold.

12. The device of claim 11, wherein the second polymer is at least one selected from the group consisting of fibrin glue, gelatin, collagen, alginate, cellulose, pectin, Matrigel, and silk fibrils.

13. The device of claim 11, wherein the second polymer is covalently linked to the at least one agent.

14. The device of claim 11, further comprising a second hydrogel comprising a third polymer and a second population of cells,
wherein the second hydrogel is separated from the first hydrogel via at least one microporous membrane,
wherein the at least one microporous membrane is configured to block contacting of the second population of cells in the second hydrogel with the first population of cells while allowing an exchange of non-cell contents between the first hydrogel and the second hydrogel.

15. The device of claim 14, wherein the second population of cells are non-dividing cells.

16. The device of claim 14, wherein the second population of cells comprise transfected or transduced cells harboring at least one expression vector containing at least one nucleic acid sequence encoding at least one protein or peptide.

17. The device of claim 14, wherein the third polymer is at least one selected from the group consisting of fibrin glue, gelatin, collagen, alginate, cellulose, pectin, Matrigel, and silk fibrils, and is different from the second polymer.

18. The device of claim 1, further comprising at least one rigidifying structural element configured to stabilize, immobilize, shape, and/or form-fit the device at the injury site following the application of the device to the injury site.

19. The device of claim 18, wherein the at least one rigidifying structural element is at least one selected from the group consisting of a pin, a stent, a screw, a plate, a bar, a cast, and a splint.

20. The device of claim 1, wherein the scaffold comprises the at least one putrescine-modified first polymer.

* * * * *